United States Patent [19]
Hersh

[11] Patent Number: 5,827,886
[45] Date of Patent: Oct. 27, 1998

[54] COMPOSITION FOR RELIEF OF ARTHRITIS-INDUCED SYMPTOMS

[75] Inventor: Theodore Hersh, Atlanta, Ga.

[73] Assignee: Thione International, Inc., Atlanta, Ga.

[21] Appl. No.: 852,612

[22] Filed: May 7, 1997

[51] Int. Cl.⁶ .................. A61K 31/195; A61K 33/04; A61K 31/16; A61K 31/615
[52] U.S. Cl. .................. 514/562; 424/702; 514/561; 514/627; 514/162; 514/165; 514/171; 514/474
[58] Field of Search .................. 424/702; 514/561, 514/562, 627, 162, 165, 171, 474

[56] References Cited

U.S. PATENT DOCUMENTS

| | | | |
|---|---|---|---|
| 5,032,384 | 7/1991 | Yeh et al. | 424/49 |
| 5,667,791 | 9/1997 | Hersh et al. | 424/401 |

*Primary Examiner*—William R. A. Jarvis
*Attorney, Agent, or Firm*—Malcolm B. Wittenberg

[57] ABSTRACT

A composition and method of using it for ameliorating inflammatory reactions and painful and other symptoms of the diseases of arthritis, lumbago, low back pain, myalgias and neuralgias. The composition includes reduced glutathione, a selenoamino acid and an anesthetic, such as capsaicin, in a suitable carrier for topical application.

19 Claims, No Drawings

COMPOSITION FOR RELIEF OF ARTHRITIS-INDUCED SYMPTOMS

TECHNICAL FIELD OF THE INVENTION

The present invention deals with the combinations of several synergistic antioxidants, including enzymatic co-factors with analgesics such as capsaicin or the local caine anesthetics and anti-inflammatory agents in appropriate delivery vehicles employed in topical carriers as a means of ameliorating the inflammatory reactions and painful symptoms of a variety of arthritis syndromes, spinal pain, lumbago, myalgias and neuralgias and exercise and sport injuries. These clinical entities result primarily or secondarily from free radical damage to particular surfaces (joints and associated musculo-skeletal structures) resulting from a variety of inflammatory pathologies. A classic example is the process of "hypoxic-reperfusion injury" of rheumatoid arthritis where the etiologic factor is unknown but the free radical species and other products derived from the neutrophils "oxygen burst reaction" contribute to the joint's injury. All of these etiologies engender free radicals in joint spaces and contiguous cutaneous and musculo-skeletal tissues, requiring additional local antioxidant compositions to the therapeutic armamentarium of each disease state to aid in the amelioration of signs and symptoms and repair of the affected tissues. The synergistic locally applied antioxidants plus capsaicin as a depletor of substance P which is the major neuronal chemomediator of painful stimuli are thus adjuncts in the management of inflammation and pain in these clinical entities.

BACKGROUND OF THE INVENTION

There are a number of rheumatologic and neurologic disorders as well as clinical musculo-skeletal syndromes where free radicals play a primary or secondary role in the clinical signs and symptoms of these distinct entities. Exercise, whether as calisthenics, weight lifting, swimming, running or jogging, generates free radical species. Exercise may be followed by muscle strain and aches or sprains, or result in painful sport injuries. The most common diseases affecting joints are rheumatoid arthritis and osteoarthritis. The former is an autoimmune disease where the articular inflammation in part leads to the generation of free radicals causing further inflammation and damage to the lining (synovium) of the affected joints. Free radicals also arise in rheumatoid arthritis and the other autoimmune related diseases, as periarteritis, lupus and scleroderma, through the mechanism of ischemia-reperfusion, similar to that in myocardial damage from coronary artery disease. The common syndromes of low back pain, fibrositis, and other neuromuscular entities cause chronic pain from local inflammation. Thus, locally administered synergistic antioxidants play a role as adjuvant therapy alone or in combination with anti-inflammatory and analgesic medications, including topical capsaicin.

To follow first are some definitions of free radicals, the clinical conditions and the antioxidant defense system which the body utilizes to scavenge and neutralize the deleterious free radicals. The present invention utilizes the synergistic and complementary antioxidants most similar to those endogenous human defense mechanisms.

Free radicals are defined as atoms, ions or molecules which contain an unimpaired electron. In the body, free radicals are unstable and have short half-lives. Free radicals originate from many sources and metabolic reactions in the tissues including aerobic respiration in cells and microorganisms, cytochrome P450 catalyzed monooxygenation reactions of drugs and xenobiotics, and ionizing radiation. There are countless free radicals produced in metabolic processes, with reactive oxygen species ($O_2$, OH, $H_2O_2$) the most biologically abundant. Other free radicals include lipid hydroperoxides and carbon centered, peroxy, and phenoxy and semiquinone radicals.

Antioxidants are compounds that when present in cellular structures or chemical mixtures wherein there are biological oxidizable substrates can prevent or delay the oxidation of the substrate biological molecules. Antioxidants can act by scavenging biologically important reactive free radicals or other reactive oxygen radicals. Antioxidants in tissues may also prevent the formation of free radicals.

Another function of antioxidants is to catalytically convert the free radicals or other reactive oxygen species to a less reactive species. These body defenses may be antioxidant enzymes while others are small molecule, non-enzymic antioxidants. Antioxidants are categorized by their activities as preventive or reparative antioxidants. The advantage of using these endogenous antioxidants in topical preparations is that the product provides locally the necessary and synergistically compatible antioxidants to exert a preventive, ameliorating or therapeutic function. In order to maintain normal cellular and tissue function and integrity of organ, there needs to be a local intracellular as well as extracellular balance between the generation of free radicals (reactive oxygen species) and corresponding enzymatic and non-enzymatic antioxidant defenses. When the balance shifts to a "net" increase in oxidant levels, cell damage ensues; conversely, when net levels of oxidants decrease, either through lower generation of reactive oxygen species and/or increases in antioxidant defenses, cellular integrity and function may be maintained.

Capsaicin is the major constituent and pungent principle in the fruit of various chile peppers, each species with varied properties. Capsaicin chemically is trans-8-methyl-N-vanillyl-6-nonenamide. Capsaicin has been used as a counterirritant in various medicinal preparations to soothe irritated skin and diminish pain of a variety of inflammatory conditions including but not restricted to arthritis, osteoarthritis, myalgias, neuralgias, lumbago, low back pain, etc. Capsaicin's effect on pain relief has been ascribed to its ability to deplete and prevent re-accumulation of substance P from local sensory nerve terminals. Substance P, a neuropeptide, is the most important chemomediator of noxious stimuli from the periphery to the central nervous system. Thus, capsaicin locally depletes the affected area of substance P alleviating pain. Unlike its sole presence in some popular pain creams currently on the market, capsaicin preparations should not be the only ingredient for therapy of chronic painful and inflammatory conditions. Capsaicin should be considered as an adjunct to other local therapeutic approaches, as in these formulations.

Capsaicin, for topical medicinal purposes, is obtained from the dried fruits of the botanical family of capsicum, particularly *C. frutescens L.* and *C. annum L.*, in conformance with applicable standards of the federal Food, Drug, and Cosmetic Act. Capsaicins are commercially available for cosmetics by suppliers such as Kalsec Inc. of Kalamazoo, Mich. Because the capsaicinoids are extremely pungent and irritating in high concentrations, MSDS should be obtained and precautions observed during their preparation. Use of capsaicin is restricted to a range of 0.025% to 0.075% by weight.

A number of clinical studies have been reported on the beneficial effects of capsaicin in the various diseases and syndromes herein mentioned. Recent reviews of the clinical applications of capsaicin as an adjuvant analgesic in pain management have been reported. In dealing with arthritis, researchers have reported a significant reduction of the severity of knee pain in patients with both osteoarthritis and rheumatoid arthritis treated with topically applied 0.025% capsaicin. Another study showed significant reduction of pain and tenderness of the hands with capsaicin 0.075% only in patients with osteoarthritis. In other studies in rheumatoid patients, topical capsaicin has caused greater reductions of synovial fluid inflammatory mediators, such as substance IL-6 and prostaglandin E, during and after topical treatment than using control vehicle cream. Researchers have editorialized that capsaicin exerts an anti-inflammatory reaction by enhancing migration of phagocytes without the generation of superoxide anion and by reducing neurogenic inflammation. When capsaicin is chronically administered, it enhances chemotaxis and increases collagenase production.

Capsaicin has also been used in patients with various types of neuralgias and neuropathies. These have included patients with post-herpetic neuralgia, postmastectomy pain syndrome and diabetic neuropathy. Other studies outline its use in other musculo-skeletal and rheumatologic syndromes, including the very common entity referred to as low back pain syndrome.

In patients with acute onset or flareups of arthritis, inflammation of the synovia with development of joint fluid occur consequent to the accumulation of polymorphonuclear (PMN) leukocytes in response to a specific pathogenic stimulant or agent and/or a responsible pathogen in the infectious type of arthritis (e.g. gonorrhea, tuberculosis, bacteria, etc.). The PMN's function is to combat the deleterious agents or putative micro-organisms, which cause a release of hydrogen peroxide and various enzymes, as myeloperoxidases, into the extracellular fluids (synovial space). In the case of arthritis, the enzyme is able to catalyze hydrogen peroxide in the presence of chloride ion forming the strongly reactive species hypocholorous acid. HOCl then oxidizes tissue components and plasma protease inhibitors. Locally, as in the synovia, oxidation and inactivation of these protease inhibitors leads to protein destruction (proteolysis) which result in extreme cellular and tissue damage.

Oxidative damage has been demonstrated within the inflamed human joint by a radical mediated mechanism which is termed "hypoxic reperfusion injury." This mechanism involves the production of reactive oxygen species causing tissue damage and subsequent persistence of the inflammation of the synovial lining of the joint. Assessment of reactive oxygen species and lipid peroxidation is possible in human joint fluid (effusion) by the identification of both known intermediates and end products of these reactions.

Lipid peroxidation is a reactive oxygen species mediated pathophysiologic process which leads to cell membrane damage which in turn results in cellular dysfunction or cell death. This process is initiated by the more potent free radicals such as alkoxyl, peroxyl and hydroxyl radicals. This lipid peroxidation can lead to an autocatalytic process, since these radicals, particularly peroxyl, have the ability both to initiate and to propagate lipid peroxidation. Small amounts of free radicals, particularly the hydroxyl radical, may trigger this pathologic process. Also, the generation of superoxide radicals by any source, in the presence of iron ions further leads to formation of hydroxyl radicals with consequent start of the lipid peroxidation reaction. Such iron has been detected in human synovial fluid and has also been shown to initiate this peroxidation within the joint. Hypoxic-reperfusion injury is described as a pathophysiologic process which generates oxygen reactive species after a transient episode of ischemia on restoration of the blood supply (so-called reperfusion) to the affected tissue. Free radicals are then produced herein by the uncoupling of a variety of intracellular redox systems, leading, as aforementioned, to tissue damage. Studies in vivo have shown that the inflamed human joint with an effusion of diverse etiologies, has the propitious environment to sustain a hypoxic-reperfusion injury. Exercise causes an increase in intra-articular pressure significantly above capillary perfusion pressure, thereby resulting in occlusion of the synovial capillary bed and thus hypoxia of the joint's tissues. These events do not occur in the normal joint. Various clinical studies have demonstrated that lipid peroxidation occurs within the inflamed human joint, by assaying aspirates of synovial fluids from control (normal) subjects and those with rheumatoid arthritis. One study correlated the presence of products of lipid peroxidation in effusions and in sera with the activity of the disease. In order to prevent or ameliorate the damage caused by free radicals, the enzymatic and non-enzymatic biologic processes come into play as multiple defense systems. The former include intra and extracellular superoxide dismutase, catalase, and selenium dependent glutathione peroxidase, iron and copper binding proteins, albumin and the exogenous vitamin scavengers, ascorbic acid and alpha tocopherol. Animal studies with experimentally induced inflammatory arthritis have shown beneficial effects of the antioxidants so tested. Clinically, the so-called anti-rheumatic drugs may exert their therapeutic effects by acting as antioxidants. Nonsteroidal anti-inflammatory drugs, as those listed in this patent, act as free radical scavengers, thus pointing to the usefulness of the network of synergistic endogenous and exogenous antioxidants in locally ameliorating the reactions of the reactive oxygen species and of lipid peroxidation and thereby amelioration of the inflammatory joint response and curtailing clinical signs and symptoms of arthritis.

In disease states in humans, there is usually increased formation of free radicals, that is, reactive oxygen species which occur secondary to the etiologic disease process, but also contributory to local injury (examples: lung damage in adult respiratory distress syndrome and joints in rheumatoid arthritis). Oxygen free radicals attack cell structures, are cytotoxic and have been implicated in the pathogenesis of various disease states. Reactive oxygen species are generated continuously in vivo at chronically inflamed sites, such as the human joint in various arthritides, such as rheumatoid arthritis, systemic lupus erythematosus, osteoarthritis and others. The arthritic joint as a site of oxidative stress, an overproduction of free radicals, exceeds the inherent, local antioxidant capacity thereby causing damage. Enhanced anti-inflammatory and antioxidant support may be provided by oral, parenteral or local topical compositions as described herein. These result, as stated, in reduction of free radicals and their damage by the scavengers as well as reduction of the inflammatory synovial response. The complex cascades that comprise the inflammatory reaction occur primarily to limit tissue damage and prevent or inhibit infections.

Lipid peroxidation, as noted, is a radical mediated chain reaction which results in the alteration of polyunsaturated fatty acids which contain more than two covalent carbon-carbon double bonds. These may occur within the LDL carrier of lipids in plasma. Similar lipid peroxidation occurs in the fatty acid constituent of lipid membranes, both forming cytotoxic aldehydes. Lipid products arising from free radical attack to lipids in human joints play a role in the pathogenesis of rheumatoid arthritis.

There are a number of investigative studies which document free radical generation and damage in patients with inflammatory joint disease. Researchers have shown low levels of alpha-tocopherols in joint effusions of patients with rheumatoid arthritis consistent with its consumption to block the joint's process of lipid peroxidation. Others have shown that serum of rheumatoid arthritis patients had lower vitamin C levels, evidencing existence of a redox stress. Researchers have correlated a risk factor for development of this disease in cases which exhibited low serum antioxidant levels.

Imidazole derivatives have been proposed as protective agents in U.S. Pat. No. 5,525,621, the disclosure of which is incorporated by reference. It was shown that singlet oxygen is one of the most destructive free radical species in the lesion of ischemia/reperfusion. These imidazole compounds are able to scavenge singlet oxygen and therefore like other scavengers are of value for the protection of tissues exposed to this pathologic process during inflammatory conditions due to the damage induced by singlet oxygen.

The importance of reduced glutathione (GSH) in protecting cells and aerobic organisms against oxidative stress by its ubiquitous nature and role as an antioxidant has been well established. However, GSH in this role is itself oxidized (GSSG). Thus, glutathione metabolism needs to act in combination with other enzyme systems in order to again reduce the glutathione molecule to GSH so it may renew its role as a free radical scavenger. Indeed, a few examples of these intricate metabolic processes can be cited.

GSH functions coordinately with the enzyme glutathione peroxidase to break down hydrogen peroxide and lipid hydroperoxides. Glutathione peroxidase requires selenium as a co-factor so that locally GSH and glutathione peroxidase and selenium may function synergistically at the injured site both as free radical scavengers and equally important in the repair process of radical-mediated biological damage. Radical scavenging by GSH results in a superoxide dependent chain sequence whereby the GSH, as already noted, is oxidized to GSSG and the $O_2$ is reduced to hydrogen peroxide ($H_2O_2$). If this reaction was to occur intra cellularly uninterruptedly, the concentrations of the latter two would be excessive and more damaging than the initial oxidizing event, theoretically placing the cell under oxidant stress because of need to reduce the levels of GSSG. Thus, protection occurs in cells because of other factors or enzymes which like superoxide dismutase (SOD) occur concomitantly intra cellularly with glutathione. SOD catalyzes the reaction of free oxygen radical plus hydrogen ion to produce oxygen and hydrogen peroxide. Thus, SOD prevents radical mediated chain oxidation of GSH, thereby allowing GSH to function physiologically as a free radical scavenger again without creating or causing oxidative stress to the cell. The present invention thus contemplates as a preferred embodiment adding SOD in sufficient concentrations and in protective delivery vehicles, such as liposomes, so that it plays its role locally as a catalytic enzyme but also to synergize with glutathione, effectively so that the SOD protects GSH against radical-mediated chain oxidation and the combination of SOD and GSH preventing redox cycling reactions. This association is vital and beneficial for it allows glutathione to function as an efficient free radical scavenger, in synergy with other enzymes and vitamins of these cosmetic/pharmaceutic preparations.

Rheumatoid arthritis is a systemic illness with joint inflammation a paramount characteristic, most typically chronic pain and swelling of multiple joints (polyarthritis). Other criteria for diagnosis include symptoms of morning stiffness, tenderness or pain on motion of joints. Signs and symptoms usually involve symmetrical joints; that is, swelling on both sides (like knees, elbows). There are characteristic radiologic changes in rheumatoid arthritis joints and abnormal serologic agglutination tests demonstrating the presence of the rheumatoid factor.

Rheumatoid arthritis is world-wide in distribution and affects all races and ages, occurring in about two to three percent of the general population. The most consistent finding is a chronic inflammatory arthritis with a thickened synovium packed with inflammatory cells, including lymphocytes and plasma cells, which produce large amounts of immunoglobulins including rheumatoid factor. These form locally and systemically complexes with IGg immunoglobulins which play a role in the pathogenesis of the arthritis and of the extra-articular complications of the disease. As the immune complexes are formed, complement is activated initiating inflammation and chemotaxis. The polymorphonuclear cells in the joint fluid ingest the pathogenic complexes. These white blood cells release cytosomal enzymes and free radicals into the joint (the "respiratory burst reaction") since they begin to disintegrate as they load up on the immune complexes. The released autolytic enzymes and free radical species perpetuate and markedly accentuate the inflammatory process within the rheumatoid joints. Similarly, intermediate complexes are removed from the circulation by these phagocytic white blood cells which may then precipitate in vessel walls producing local inflammation, the so-called vasculitis that affects other organs in rheumatoid arthritis. Thus, adjuncts in therapy of rheumatoid arthritis should include administration of systemic antioxidants, as well as their local application as presented herein, including pain relievers, particularly capsaicin as depletor of pain mediator substance P, and anti-inflammatory agents.

Similar pathogenesis has been described for other autoimmune diseases, where arthritis is also a frequent manifestation of the diseases. These clinical entities include systemic lupus erythematosus, periarteritis nodosa, polymyositis, scleroderma and other less common syndromes. Signs and symptoms may abate with benefit to the patient with use of these proposed synergistic antioxidant preparations.

Rheumatoid arthritis is characterized pathologically by a chronic inflammation of the articulations (joints). A serum rheumatoid factor binds to immunoglobulin G when exposed to oxygen free radicals. These complexes are formed within the synovial joint fluid and in serum stimulate the neutrophils to generate more free radical species in the affected articulations. A consequence is the depolymerization of joint hyaluronic acid and proteoglycan damage to the cartilage matrix. As noted, neutrophil's enzyme release of elastase coupled with the decreased local joint fluid activity of alpha-1-antiproteases caused by oxygen free radicals account for the chronicity of symptoms and progressive deterioration of the rheumatoid joints. Free radical scavengers tend to ameliorate the signs and symptoms of these inflammatory diseases, thus their use as synergistic antioxidants in these compositions also to relieve the pain and the inflammation by use of appropriate medications, such as capsaicin, salicylates, nsaids and corticosteroids is indicated.

Free radicals, in the presence of abnormal amounts of iron and copper may be implicated in scleroderma through fragmented scleroderma auto antigens. Scleroderma (systemic sclerosis), an autoimmune disease of unknown cause, is characterized by increased vascular reactivity and fibrosis of skin and blood vessels. The associated vascular entity of Raynaud's Phenomenon which is a temporary cessation of blood flow to extremities and internal organs, may generate free radicals through repeated episodes of ischemia followed by reperfusion. This might activate the immune system and cause the scarring of skin and other organs of scleroderma. Local and systemic antioxidants may thus be of value in preventing and ameliorating scleroderma.

At the junction of two bones, their ends are covered by a layer of cartilage within the joint. The cartilage is akin to a resilient padding which reduces friction and absorbs shock. Osteoarthritis results when this cartilage begins to deteriorate in certain areas of stress, often wearing away entirely. Bones then rub together and elicit pain, most often occurring in the hands, hips and knees (example, "housemaid's knee"). Inflammation and swelling of the affected joints may be present, followed by symptoms of joint stiffness and loss of mobility. It is estimated that 16 million Americans suffer from osteoarthritis.

The clinical pathology view of low back pain hypothesizes that it results from subtle damage to soft tissues with ensuing local inflammatory response and tissue swelling, leading to local pain. More disabling back pain may result from more severe injuries, such as trauma and acute intervertebral disk herniation. Other factors for low back pain include a chronic inflammatory response triggered by the initial inciting event and, particularly, at the workplace. The etiology of pain results from biomechanical actions such as heavy lifting, bending awkward postures or whole body vibration causing back damage from either acute or chronic insults to the back.

Work related low back pain is one of the most common occupational disorders accounting for about 25% of all worker's compensation claims and one third of all compensation costs. Ten percent of workers will stop working at a job or change jobs because of low back pain. Therapies are varied, including changing work activities, physical therapy with rehabilitation, anti-inflammatory medications by oral route or locally applied to affected area, and local manipulations and other measures as recommended by chiropractic medicine.

SUMMARY OF THE INVENTION

The present invention deals with a composition and method of reducing the inflammation and pain of various clinical entities including, but not limited to, the arthritis of rheumatoid arthritis and the other so-called autoimmune diseases, and osteoarthritis, the common syndrome of low back pain, myalgias, neuropathies, such as that of diabetes, and neuralgias, such as after shingles (herpes) as well as any cutaneous manifestations, if any, of these conditions. In addition, the compositions deal with reduction of free radicals initiated by exercise of any form and amelioration of the post-exercise signs and symptoms of muscle strain and connective tissue alterations. The composition comprises an effective amount of the endogenous antioxidant, glutathione, in its reduced form and a selenoaminoacid, such as selenemethionine or selenocysteine, which may act as both a selenium co-factor of the synergistic antioxidant glutathione peroxidase, and selenium as itself, an antioxidant. In addition, other intra and extracellular synergistic antioxidants of L-glutathione, namely, superoxide dismutase, ascorbic acid (vitamin C), acetyl-L-carnitine and glutathione reductase, the latter provided in a thiol rich extract preparation, may be employed. The preparations herein described may be in the forms of creams, lotions, solutions including sprays and aerosols and in roll-on dispensing bottles, ointments, gels, balms, patches, or emulsions as are known in this industry. The compositions may include other free radical scavengers, antioxidants, anti-inflammatory agents, and local anesthetics, particularly capsaicin, to deal with the inflammation and chronic pain characteristic of these diseases and clinical syndromes. These include but are not limited to the anti-oxidants, tocopherols (vitamin E), green tea and pycnogenols and also steroids, non-steroidal anti-inflammatories, capsaicin extract, tissue respiratory factor and the local anesthetics of the caine family.

DETAILED DESCRIPTION OF THE INVENTION

As previously noted, the present invention deals with glutathione (GSH) in combination with selenium and thiol compounds such as those containing glutathione reductase and sulphur amino acids plus other synergistic antioxidants used topically to act as free radical scavengers and neutralizers reducing inflammatory reactions in various clinical rheumatologic and musculo-skeletal entities and analgesics, such as capsaicin to diminish pain. It is proposed that the described active ingredients be employed in topical compositions. Topical carriers are employed which should be both non-irritating to the skin and which are suitable for delivering the active components to the affected areas. Further, suitable topical carriers should be those which do not inhibit the antioxidant activity of the active ingredients thus reducing the efficiency of the composition. Further, such carriers must be of sufficiently high purity and sufficiently low toxicity to render them suitable for chronic topical administration to the skin and be free of bacterial contaminants.

The topical use of anti-inflammatory agents to reduce and alleviate swelling and erythema of inflammatory lesions and the associated pain syndrome has been well established. Many topical preparations are on the market, but mainly as anti-inflammatory creams, lotions, ointments or gels. These compositions ordinarily contain steroidal anti-inflammatories, non-steroidal (salicylates and nsaids) and natural anti-inflammatories, such as extract of aloe vera. Thus, in association with the present anti-oxidants, the anti-inflammatories are incorporated to provide topical preparations in stable forms to ameliorate the inflammatory reaction as is well known in the therapeutic art of the clinical conditions. In addition, anti-inflammatories are used in these topical preparations to reduce local inflammatory reactions and pain of the various types of arthritis, myalgias, neuralgias, lumbago, low back pain and associated dermatoses of diverse various etiologies. Symptomatic relief is afforded in addition to the specific therapies for each of these entities.

Inflammatory lesions have pathologic responses which include the presence of neutrophils (leukocytes). Systemic leukocytosis may be a reflection of infection or other generalized disorders. Immunological defense mechanisms are also called into play in these inflammatory reactions. Liberation of free radicals during these inflammatory lesions of various etiologies are also accompanied by the so-called "oxidative burst" of activated neutrophils. This "oxidative burst" produces abundant superoxide radical, which is believed to be an essential factor in producing the cytotoxic effect of activated neutrophils. Providing the antioxidants in topical preparations with combinations of anti-inflammatory agents to have a wide spectrum therapeutic effect on these dermatologic, neuro-muscular, vascular and articular pathologies is an important aspect of the present invention.

A number of medications are available for the symptomatic and pathogenic characteristics of the various categories of arthritis. U.S. Pat. No. 4,619,829 (October, 1986), which is herein incorporated by reference, proposes unique vitamin combinations by oral route for long term treatment and/or prevention of rheumatic diseases. These include the B complex and other standard vitamins and minerals without defining pharmacologic or pathogenetic mechanisms for their medicinal use in these rheumatic disorders, other than as standard nutritional vitamin supplements, as is well known with nutritional and medical professionals.

Vitamin E, particularly in its alpha-tocopherol moiety, has been employed to inhibit oxidation of oils and fats in foods, cosmetic preparations and drugs. Vitamin E is not only an anti-oxidant but also has anti-inflammatory properties. In skin, vitamin E levels are present in dermis and epidermis, but are depleted by malnutrition and by ultraviolet light, thus the present invention recognizes their importance in providing these to act in vivo as antioxidants, and thereby protecting affected and new skin cells. Vitamin E moisturizes and enhances skin smoothness. It is soothing and also participates in skin repair and wound healing.

Cell membranes and plasma lipoproteins contain alpha tocopherol, which is a lipid soluble molecule that functions as a chain breaking (reparative) anti-oxidant. An —OH attached to the hydrophobic structure of tocopherol easily releases its hydrogen atom, so that peroxyl and alkoxyl free radicals generated during lipid peroxidation then may combine with this anti-oxidant instead of with adjacent fatty acid side chains, thereby terminating this chain reaction process of lipid peroxidation. Experimental evidence shows that the tocopherol radical migrates to the membrane surface. It is then reconverted to alpha tocopherol by its reaction with ascorbic acid (vitamin C). Thus vitamins E and C are synergistic and minimize the toxic effects on lipid peroxidation in cell and basement membranes and lipoproteins. Moreover, glutathione and selenium also act synergistically with vitamin E, the former, GSH, by regenerating alpha tocopherol from its tocopheroxyl radical form. Also, vitamins C and E, selenium and glutathione, in experimental animals, have been shown to work together as anti-oxidants.

Alpha tocopherol (vitamin E) is preferably employed in these compositions as an in vivo antioxidant in the form of tocopherol acetate or any other of its active and protected non-oxidized forms, comprising approximately from 0.01% to 25% by weight, preferably from 0.1% to 10%, most preferably from 0.5% to 5.0%.

Ascorbic acid, vitamin C, plays a significant role in skin metabolism and in synthesis of collagen as a co-factor in hydroxylation reactions for the formation and function of collagen. High vitamin C levels not only stimulate collagen but also reverse epidermal thinning and offer skin protection against ultraviolet rays. These properties of vitamin C are enhanced by using ascorbyl glucosamine where the polyamine complex protects the ascorbic acid, enhancing the antioxidant and anti-collagenase properties of these products. It is commercially available from Collaborative Laboratories, East Setauket, N.Y.

Vitamin C, a water soluble small molecule anti-oxidant, is located in aqueous phases of cells while, as noted, vitamin E is in the lipid portion of membranes. Together they protect lipids and lipid structures against peroxidation. Vitamin C repairs the tocopheroxyl radical and permits that molecule to function again as a tocopherol free radical chain-breaking anti-oxidant. The ascorbate free radical produced in this reaction with tocopherol can be removed from the tissues by a dismutation reaction. The dehydroascorbate and the ascorbate radical can then be removed by enzyme systems that use NADH or NADPH as sources of reducing molecules. Thereby, ascorbate is recycled to protect again the process of lipid peroxidation by its synergistic function with vitamin E.

Ascorbic acid can be employed in these compositions in an amount between 0.01% to 25% by weight based upon the weight of the active ingredients, preferably from 0.1% to 10% by weight, most preferably from 1.0% to 3% by weight. Most preferably, the ascorbic acid to be used in these compositions will be protected by encapsulation, such as liposomes or nanospheres as is well known in the art by chemical bonding such as in ascorbyl palmitate or ascorbyl glucosamine. Ascorbyl glucosamine would be used in a range of 0.05% to 12% by weight based on the weight of the active ingredients, preferably from 0.5% to 9% by weight and most preferably from 1.5% to 7.5% by weight.

Thus, these topical preparations will, in their preferred form, contain mixtures of vitamins C and E to enhance locally the anti-oxidant activities of the active ingredients, particularly in their function as chain-breaking anti-oxidants in lipid peroxidation.

The present invention also contemplates, as an optional expedient, the inclusion of vitamin A which occurs only in animal organisms and is not found in plants. It is usually extracted from liver oils, mainly in its esterified forms but may also be synthesized in the laboratory. The liver converts carotenoids, particularly beta-carotene, into vitamin A in the form of vitamin A palmitate (retinyl palmitate), may be used in these preparations. This vitamin can be used in concentrations from 0.001 to 3% but more preferably from 0.1% to 2.0%, most preferably from 0.5% to 1.0% by weight. Vitamin A may also be delivered in liposomes protected from oxidizing by tocopherol acetate, as available from suppliers like Collaborative Laboratories, East Setauket, N.Y., or as Rivosome Ace from R.I.T.A. Corp. in Woodstock, Ill.

Beta-carotene, which is pro-vitamin A, is found in many plants and is a nutrition source and the main coloring matter in carrots and egg yolks. B-carotene is used in cosmetics as a coloring agent and also as a source to the body of vitamin A. Carotene, like vitamin A compounds, may be absorbed by the skin. Carotenoids, including beta-carotene, are small molecule dietary and topical anti-oxidants. Carrot oil is rich in vitamin A and carotenoids and may be used in these preparations in a concentration of at least 0.001% to 1.0% as a source of these molecules. It is a light yellow essential oil derived from seeds of carrots and has no known toxicity. Carrot seed extract, may also be used and is derived from the seed of *Daucus carota sativa*.

Wahl and co-workers at the National Institutes of Health taught methods to treat chronic inflammatory diseases including the various arthritis syndromes in U.S. Pat. No. 5,499,688 issued Sep. 12, 1995, which is herein incorporated by reference. They administered effective amounts of nitric oxide scavengers to decrease the amount of putative nitric oxide present at the site of the inflammation. These compounds belonged to complexes with L-arginine, L-canavanine, citrulline and aminoguanidine. They note, akin to the argument herein, favoring the use of antioxidants to neutralize free radicals. This '688 patent augurs a method for suppressing joint disease, inflammation, tissue swelling and bone and cartilage degradation in chronic arthritis.

Certain antioxidants, particularly the endogenous L-glutathione and superoxide dismutase, as well as the element selenium, a co-factor for the enzyme glutathione peroxidase, and thiol compounds such as L-cysteine, can be employed in suitable carriers such as lotions, solutions, creams, ointments, foundation products, balms, sprays, aerosols or gels to protect and to treat the overlying skin surface in dealing specifically with the effects of the various free radicals on biomolecules, lipids and cell membranes. Moreover, anti-inflammatory agents, topical anesthetics, and pain reliever ingredient capsaicin in appropriate concentration and delivery vehicles are to be incorporated within these free radical scavenger and pain relief preparations.

Without being bound to any particular theory, it is noted that reduced glutathione is employed in protecting cells and aerobic organisms against oxidative stress by itself being oxidized. Thus, glutathione must act in combination with other enzyme systems in order to be reduced so that it may renew its role as a free radical scavenger. GSH functions also coordinately with the enzyme glutathione peroxidase to break down hydrogen peroxide and lipid hydroperoxides. Glutathione peroxidase in the body requires selenium as a cofactor to exert its biologic antioxidant function. Selenium compounds have been shown to scavenge oxygen-centered radicals in vivo with reduced glutathione through glutathione peroxidase. It is believed that selenium-GSH peroxidase catalyzes toxic hydrogen peroxide in the presence of reduced glutathione. This reaction reduces glutathione to oxidized glutathione (GSSG). In turn, the GSSG is reduced back to GSH by the enzyme GSH reductase thereby maintaining abundant cellular GSH to scavenge free radicals anew.

In summary, the major functions of reduced glutathione (GSH) in protection against lipid peroxidation involve three types of reactions, all inter-related and synergistic in combining non-enzymic scavengers and enzymes and antioxidants as follows:

1. GSH with selenium as a co-factor for glutathione peroxidase eliminates toxic peroxides;

2. GSH reduces oxidized forms of vitamin C which, in turn, maintains vitamin E in its reduced form promoting its metabolic functions. Thus, GSH supports the free radical reductions and free radical chain-terminating functions of the two nutrient antioxidants, vitamins C and E;

3. GSH functions through glutathione s-transferases to detoxify reactive aldehydes created during the process of lipid peroxidation.

As noted, some cells have sodium dependent up-take systems for GSH, allowing cells to use both exogenous GSH and endogenously synthesized GSH, thereby enhancing a cell's ability to survive oxidative and free radical damage. In this fashion, extra-cellular GSH also protects cells' survival.

Investigative studies have shown that cell viability correlates best with GSH in mitochondria. In the absence of GSH, lipid peroxidation is uncontrolled and leads to cell injury and death. Conversely, GSH protects cells from the ravages of free radicals working synergistically with anti-oxidant enzymes and dietary vitamin antioxidants.

L-glutathione is employed in these compositions in an amount between 0.001% to 15% by weight based upon the weight of active ingredients, preferably from 0.01% to 5% and most preferably from 0.05% to 2.5% by weight.

It is further contemplated that the present composition, as a preferred embodiment may include acetyl L-carnitine. This latter component further participates in protecting cells against lipid peroxidation by locally increasing the amount of antioxidizing agents of GSH and ubiquinol. L-carnitine, also known as gamma trimethylamino-beta hydroxy butyrate or Vitamin Bt occurs naturally in the body. It is a normal endogenous intermediary metabolite which has been identified in all mammalian cells and in blood and urine. Acetyl L-carnitine is the acetyl derivative of L-carnitine and is also a naturally occurring substance in the body as it provides a transport mechanism for the acetyl groups created by the beta oxidation of fatty acids while concomitantly regenerating acetyl co-enzymes in the cytosol of the cell.

Of interest herein, acetyl L-carnitine has been shown to have a scavenging effect on the free superoxide anion. This antioxidant activity coupled by acetyl L-carnitine's effect of inducing an increase in reduced glutathione and reduced ubiquinone levels provides a stabilizing effect on membranes by decreasing membrane lipid peroxidation. Acetyl-L-carnitine is optionally employed in these compositions in dosages of at least approximately 0.001% to 5% by weight and most preferably from 0.1% to 1.0% by weight. Thus, reduced glutathione and acetyl L-carnitine in topical preparations will act somewhat synergistically; the former as an antioxidant which itself becomes oxidized and better able to be regenerated locally in its reduced form by the metabolic functions of acetyl L-carnitine.

Further, glutathione and selenium act synergistically in vivo as they are both constituents of the same enzymatic system. GSH serves as a specific donor substrate while selenium, provided from alimentary sources or locally from topically applied preparations of selenoamino acids, as herein mentioned, or selenium yeast extracts provide the prosthetic group of GSH peroxidase, during its synthesis. The glutathione and selenium antioxidant functions are intrinsically related since by keeping a peroxidase in action, the GSH and selenium contribute to the removal of the dismutation product of free oxygen radicals, namely, hydrogen peroxide. In a broad sense, GSH and selenium modulate free radical chains initiated or sustained by hydroperoxides.

Selenium is also used in the present invention for its role as an antioxidant. Selenium is an essential trace element, and a cofactor and constituent of the enzyme glutathione peroxidase. Selenomethionine decomposes lipid peroxides and inhibits in vivo lipid peroxidation in tissues of vitamin E deficient chicks. Other selenoproteins also show a high degree of inhibition of lipid peroxidation in hepatic tissues of various species, thus concluding that in vivo selenium displays antioxidant behavior. Selenium has also been shown to affect the immune system and decrease the development of various malignancies.

Selenomethionine is employed in these compositions in an amount between at least 0.001% to 10% by weight based upon the weight of the active ingredients, preferably from 0.005% to 5%, most preferably from 0.01% to 2% by weight. Selenium as, for example, a selenium yeast extract, may be employed in these compositions comprising from approximately 0.01 to 10% by weight, preferably from 0.1% to 7.5% by weight, most preferably from 1.0% to 5% by weight.

Yeast extracts with mineral glycopeptides and amino acids, such as selenomethionine or zinc glycopeptide and copper have already been mentioned as optional, yet significant, components of these preparations. An additional product which may be part of the active ingredients of these compositions are sulphur rich yeast extract compounds, also commercially available (example: Clariskin, R.I.T.A. Corporation, Woodstock, Ill.). This material, rich in glutathione and glutathione reductase, is extracted from the cytoplasm of eukaryotic cells of *Saccharomyces cerevisiae*. This sulphur rich yeast with the antioxidant glutathione and the associated enzyme, glutathione reductase, has the intra-cellular function of reducing glutathione (GSSG) that has already been oxidized to its role again as an antioxidant as reduced glutathione (GSH). This reaction can be shown as

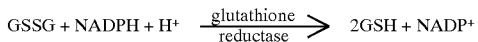

Thus, the glutathione reductase in these thiol yeast extracts, as aforementioned, participates in the enzymatic reaction toward production of GSH, thus enhancing the anti-free radical activity of these complex and synergistic compounds. This composition with its high content of glutathione reductase can comprise at least 0.01% by weight up to 4.0% of these preparations, preferably 0.05% to 2.0% and most preferably from 0.1% to 1.0%.

As noted previously, the active ingredients described above can be incorporated in any suitable pharmacologically acceptable carrier which is suitable for topical administration to the human skin. As such, the pharmacologically acceptable carrier must be of sufficient purity and have sufficiently low toxicity to render it suitable for administration to a human. The carrier may represent a major portion of the total composition from at least approximately 80%.

Typical compositions for use herein include a wide variety of physical forms. These include, but are not limited to, solutions, lotions, creams, oils, gels, sticks, sprays, ointments, balms, patches and pastes. Generally, such carrier systems can be described as being solutions, emulsions, gels, solids as ointments and aerosols or sprays.

Solvents are generally employed in the preparation of suitable topical compositions. Such solvents can either be aqueous or organic based and, in either case, the solvent must be capable of having dispersed or dissolved therein the above-described active components while not being irritating to the user. Water is a typical aqueous solvent while suitable organic solvents include propylene glycol, butylene glycol, polyethylene glycol, polypropylene glycol, glycerol, 1,2,4-butanetriol, sorbitol esters, 1,2,6-hexanetriol, ethanol, isopropanol, butanediol and mixtures thereof. Solvents can be included in the overall composition in amounts ranging from 0.1% to 99% and preferably from 2.0% to 75%. It is noted that compositions of the present invention can be produced in the form of an emollient. A wide variety of suitable emollients are known and may be used herein. In this regard, reference is made to U.S. Pat. No. 5,296,500, the disclosure of which is incorporated by reference.

Alternatively, the present composition can be formulated as a lotion containing from about 0.01% to 15% of the above described active ingredients. Further, the product can be formulated from a solution carrier system as a cream. A cream of the present invention would preferably comprise from about 0.1% to 15% and preferably from 1% to 5% of the above described active ingredients. Lotions and creams can be formulated as emulsions as well as solutions. These can be presented in roll-on bottles to avoid handling the anesthetic-containing compositions.

It is contemplated that as one embodiment, the active ingredients described above be used as a lotion or cream emulsion of the oil-in-water type or as a water-in-oil type, both of which being extremely well known in the cosmetic field. Multi-phase emulsions such as the water-in-oil type are disclosed in U.S. Pat. No. 4,254,105, the disclosure of which is incorporated herein by reference.

It is further contemplated that the active ingredients of the present invention be formulated from a solution carrier system as an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from 1% to 95% of an emollient plus to about 0.1% to 90% of a thickening agent. Reference is again made to U.S. Pat. No. 5,296,500 and the citations contained therein for a more complete disclosure of the various ointment, cream and lotion formulations for use herein.

As further noted from several of the examples, the present invention further contemplates the use of additional optional expedients, for example, superoxide dismutase (SOD). SOD is a ubiquitous cellular enzyme whose main function is in protecting cells against oxidative stress. Superoxide dismutases are a family of cytosolic metaloenzymes which specifically remove free oxygen radical ($O_2$). There are three distinct forms of SOD, namely, CUZN SOD, MN SOD and extracellular SOD (EC—SOD) which is a copper enzyme located on endothelial cell surfaces. The differences in the SODs is in their aminoacid sequences as well as location at their active sites of the transition metals. It is hypothesized that the enzyme SOD, along with glutathione peroxidase and its selenium cofactor are effective preventive antioxidants because they eliminate molecules involved in the initiation of free radical reactions. SOD also protects intracellular reduced glutathione against radical mediated chain oxidation as the combination of SOD and reduced glutathione prevents redox cycling reactions.

As stated, free radical scavenging activity by GSH in a superoxide dependent chain sequence, intracellularly, and ensuing glutathione molecules and $H_2O_2$ would exceed a first oxidizing event and result in damage. Thus, the association of GSH with SOD is vital to preventing this sequence. Free radical scavenging by GSH may also result in thiyl radicals (GS) which then give rise to superoxide which may then be catalyzed by SOD.

Superoxide dismutase can be employed in these compositions in an amount comprising approximately 0.01% to 15% by weight, preferably 0.1% to 10%, most preferably 0.5% to 5%. Most preferably, superoxide dismutase will be employed in these compositions in an encapsulation, such as liposomes as is well known in the art. As superoxide dismutase in liposomes, the amounts comprised in these compositions will range from at least 0.01% to 5% by weight, most preferably from 0.1% to 2%.

It is also contemplated that, as a further optional expedient that the present composition optimally contain from approximately 0.01% to 10% Japanese green tea. Chemically, extracts of Japanese green tea have been analyzed and characterized. Active ingredients include caffeine, theobromine, theophylline and xanthines which, together, have been shown to reduce irritation. Green tea also contains potent polyphenols, catechin compounds, which effectively act as antioxidant agents to scavenge for radicals. The main catechin constituent of green tea is (—)epigallo catechin gallate (EGCG). It has also been shown that EGCG inhibits hydrogen peroxide formation by human leukocytes, the first cell in the inflammatory cellular response to injury. EGCG is of value to function synergistically as an exogenous antioxidant in these topical preparations with the active ingredients comprised of endogenous antioxidants.

Green tea can optionally be employed in these compositions in amounts from approximately 0.01% to 10% by weight, preferably 0.1% to 5% by weight, most preferably 0.5% to 2.5% by weight. Green tea may also be used in encapsulations such as glycospheres from at least a concentration of 0.01% by weight.

The following examples are presented to illustrate the present invention:

EXAMPLE 1

The following formulation is directed to the making of a cream for topical application employing the active ingredients of the present invention.

| Ingredient | Percent by Weight |
| --- | --- |
| Phase I (add together and heat to 65°) | |
| water | 59.845 |
| hydroxyethylcellulose | .8 |
| EDTA | .08 |
| Phase II (add to stirring Phase I) | |
| carbomer | .1 |
| water for carbomer slurry | 3.3 |
| Phase III (add to stirring Phase I/ Phase II) | |
| PEG 7 glycerol cocoate | .15 |
| Phase IV (add together, heat to 75 degrees) | |
| sesame oil | 7.4 |
| canola oil | 6.4 |
| squalene oil | 1.8 |
| cetearyl alcohol | .2 |
| cetearyl alcohol polysorbate | .2 |
| stearic acid | 3.1 |
| cetyl alcohol | 2.4 |
| cetyl ricinoleate | 1.8 |
| phenyldimethicone | 1.1 |
| arnica oil | 1.0 |
| sodium hydroxymethylglycinate | .3 |
| cocoa butter | .1 |
| triethanolamine 99% | .3 |
| lecithin | .6 |
| Phase V (allow above mixture to cool to 40° C., then add below mixture) | |
| sodium PCA | .3 |
| green tea | 1.0 |
| seaweed | 1.5 |
| sodium hyaluronate | .2 |
| vitamin B5 - dexpanthenol | .5 |
| selenomethionine | .5 |
| ascorbyl glucosamine (vitamin C) | 2.6 |
| pseudocollagen | .9 |
| carrot oil | .1 |
| Germaben II (propylene glycol, diazolidinyl urea, methyl paraben, propyl paraben) | 1.1 |
| L-glutathione | .1 |
| superoxide dismutase | .15 |
| capsaicin | .075 |
| | 100.% |

EXAMPLE 2

The following formulation is directed to the making of a lotion for topical application employing the active ingredients of the present invention.

| Ingredient | Percent by Weight |
| --- | --- |
| Phase I (add together and heat to 65°) | |
| water | 58.10 |
| EDTA | .075 |
| hydroxyethylcellulose (HR250) | .5 |
| Phase II (add to stirring Phase I) | |
| carbomer ETD 2050 | .090 |
| water for carbomer slurry | 3.33 |

-continued

| Ingredient | Percent by Weight |
| --- | --- |
| Phase III (add to stirring Phase I/ Phase II) | |
| PEG 7 glycerol cocoate | .14 |
| Phase IV (add together, heat to 75° and add to mixing phases I, II, III) | |
| canola oil | 10.92 |
| squalene oil | 1.0 |
| stearic acid | 3.40 |
| cetyl alcohol | 3.1 |
| cetyl ricinoleate | 1.90 |
| phenyldimethicone | 1.90 |
| PEG 10 soya sterol | .14 |
| sesame oil | 4.60 |
| cocoa butter | .90 |
| triethanolamine, 99% | .31 |
| Na Hydroxymethylglycinate | .06 |
| lecithin | .6 |
| Phase V (allow above mixture to cool to 40°, then add below mixture) | |
| niacinamide | .4 |
| sodium PCA | .5 |
| marine algae | 1.5 |
| NaHyaluronate | .53 |
| echinacea | .1 |
| dex-panthenol (vitamin B5) | .5 |
| thiol yeast extract | .50 |
| Germaben II | 1.0 |
| ascorbyl glucosamine (collaborative) | 2.60 |
| pseudo collagen | .2 |
| carrot oil | .05 |
| zinc glycopeptide | .2 |
| green tea | .5 |
| superoxide dismutase | .15 |
| selenomethione | |
| acetyl-l-carnitine | .03 |
| L-glutathione | .10 |
| capsaicin | .075 |
| | 100.00% |

EXAMPLE 3

The following is an example of a pain relief capsaicin-containing composition employed as a lotion in a roll-on deodorant-type bottle:

| Ingredient | Percent by Weight |
| --- | --- |
| L-glutathione | 0.1% |
| selenomethionine | 0.05% |
| superoxide dismutase | 0.15% |
| In liposomes | |
| Japanese green tea | 1.0% |
| arnica oil | 0.75% |
| ascorbyl glucosamine (vitamin C) | 2.64% |
| tocopherol acetate (vitamin E) | 0.5% |

The base for the inactive ingredients include water, a cosmetic fluid preparation such as DOW 200 fluid, gums such as Lipocol S12 and S-22, imidurea, methyl paraben and propyl paraben.

In the various embodiments of this invention, numerous examples have been cited. It is clearly noted that products using capsaicin as the preferred anesthetic administer a dose of capsaicin extract ranging from 0.025% to 0.075%. Thus, it is understood that in these preparations of synergistic antioxidants with capsaicin, the dose employed of the latter may be one of the other standard doses, i.e. 0.025% or 0.05%. Similarly, some of the active principles may be administered in encapsulation form, such as liposomes, nanospheres or glycospheres. These would pertain to vitamins A, C and E and green tea and all are commercially available from various national manufacturers, each product with a specific range of % by weight of active ingredients, as aforementioned. Likewise, selenomethionine may be substituted by selenocysteine or other selenoglycopeptides, such as selenium yeast extract, wherein its concentration would range from at least 0.01% to 1.0%.

EXAMPLE 4

SALYCYLIC ACID OINTMENT WITH ANTIOXIDANT COMPLEX

| Ingredient | Percent By Weight |
| --- | --- |
| cetyl alcohol | balance |
| oleyl alcohol | 30.0 |
| propylene glycol | 25.0 |
| Germaben II | 1.0 |
| salicylic acid | 3.0 |
| L-glutathione | 0.10 |
| L-selenomethionine | 0.10 |
| superoxide dismutase | 0.20 |
| ascorbyl palmitate | 2.00 |
| tocopheryl acetate | 1.00 |
| carrot oil | 0.20 |
| green tea | 0.50 |
| dex panthenol | 0.75 |

Salicylic acid and its derivatives are inhibitors to the prostaglandins and thus lessen inflammatory reactions. Topical preparations can be used to reduce local skin inflammation as well as alleviating inflammation in incidents of trauma and various other conditions associated with free radicals and inflammation such as disorders of joints, bursa, muscles and tendons.

The aforementioned is a prototype example of an ointment with the synergistic antioxidant complex to fight free radicals. This composition can also be made with the addition of capsaicin 0.025% to 0.075% to reduce the pain mediator, substance P, and/or with the addition of local anesthetics of the caine family, such as benzocaine in percents ranging from 0.10% to 5.0%, most preferably from 0.5 to 1.0. Reller and Kretschmar taught the use of analgesic and anti-inflammatory compositions, particularly salicylic acid for topical applications in U.S. Pat. No. 4,199,576, (Apr. 22, 1980), which is herein incorporated by reference. Also included herein by reference is U.S. Pat. No. 5,612,321 (Lin and Baier - Mar. 18, 1997) which teaches that panthotenic acid in combinations with salicylic acid renders the topical compositions less irritating to the skin.

EXAMPLE 5

Ointment

Accepted formulations for ointments will include state-of-the-art ingredients including, as an example, a base of Japan wax or white wax, 15–22%, stearyl alcohol, 18–20%, white petroleum 5–8%, polyoxethylene monoleate 0.1% to 0.5%, glycerin monostearate 0.2% to 0.5%, and Vasoline to balance formula. Also added is carrot oil (0.2%), arnica oil (0.75%) and antioxidant green tea (0.5%). These ingredients in the oil phase are mixed and dissolved at 70° C. As the oil phase begins to cool, add the active ingredients to the oil part and the mixture is uniformly emulsified by homogenizing. The desired texture of the ointment is obtained as it cools.

| Ingredients | Percent By Weight |
| --- | --- |
| L-glutathione | 0.1 |
| selenomethionine | 0.05 |
| ascorbyl palmitate | 1.5 |
| tocopherol acetate | 1.0 |
| superoxide dismutase | 0.1 |
| acetyl-L-carnitine | 0.03 |
| capsaicin | 0.025 |

EXAMPLE 6

Anti-Inflammatory and Capsaicin Analgesic Gel

Gels may be prepared with the synergistic antioxidant complex by combining standard gel bases utilizing conventional techniques as are well known in the industry. Many gel preparations include ethanol in concentrations ranging from 25 to 50% and polyacrylamide and acrylamide co-polymers in concentrations ranging from 0.5% to 5.0% and glycerol at 1.0 to 3.0%.

In addition to the antioxidant complex disclosed herein, the gel may contain menthol in concentrations of 0.01% to 0.1% or steroids, like hydrocortisone in concentrations from approximately 0.01 to 1.0% or anti-inflammatories such as ibuprofen, indomethacin, sulindac and naproxen in effective, safe and therapeutic amounts as established in pharmaceutical preparations well known in this industry. Although ethanols may be used in topical gel compositions, these preparations may optionally be made without alcohol and contain standard gelling compounds together with the antioxidant complex. Such an example would also be prepared by combining standard components utilizing usual conventional mixing formulations and techniques. Salicylates, steroidal salicylates and non-steroidal anti-inflammatory agents may be optional ingredients in the compositions of this invention as are well known in the art. Many of these well known anti-inflammatories are enumerated in various patents, including U.S. Pat. No. 5,384,115 by Bissett and co-workers (Jan. 24, 1995) which is herein incorporated by reference.

I claim:

1. A topical composition for ameliorating inflammatory reactions and symptoms of the various diseases and syndromes of arthritis, lumbago, myalgias and neuralgias and post-exercise symptoms and low back pain syndrome comprising reduced glutathione, a selenoamino acid and an anesthetic in suitable quantities to reduce inflammation and chronic pain characteristic of said diseases in a suitable carrier for topical application.

2. The composition of claim 1 wherein said anesthetic comprises a member selected from the group consisting of capsaicin, salicylates, non-steroidal anti-inflammatory agents and steroids.

3. The composition of claim 1 further comprising superoxide dismutase.

4. The composition of claim 1 further comprising ascorbic acid (vitamin C).

5. The composition of claim 1 further comprising alpha-tocopherol (vitamin E).

6. The composition of claim 1 further comprising acetyl-L-carnitine.

7. The composition of claim 1 further comprising glutathione reductase.

8. The composition of claim 1 wherein said selenoamino acid comprises a member selected from the group consisting of selenomethionine and selenocysteine.

9. The composition of claim 1 wherein said anesthetic comprises a non-steroidal selected from the group consisting of salicylates and non-steroidal anti-inflammatory drugs.

10. The composition of claim 1 further comprising vitamin A palmitate.

11. A method of ameliorating inflammatory reactions and symptoms of the diseases of arthritis, lumbago, low back pain, myalgias and neuralgias and post-exercise syndromes comprising topically applying active ingredients in a suitable topical carrier to an area of the body in which said symptoms are manifested, said active ingredients comprising reduced glutathione, a selenoamino acid and an anesthetic in suitable quantities to reduce inflammation and chronic pain characteristic of said disease.

12. The method of claim 11 wherein said anesthetic comprises a member selected from the group consisting of capsaicin, salicylates, non-steroidal anti-inflammatory drugs and steroids.

13. The method of claim 11 further comprising superoxide dismutase.

14. The method of claim 11 further comprising ascorbic acid.

15. The method of claim 11 further comprising acetyl-L-carnitine.

16. The method of claim 11 further comprising glutathione reductase.

17. The method of claim 11 wherein said selenoamino acid comprises a member selected from the group consisting of selenomethionine and selenocysteine.

18. The method of claim 1 1 wherein said anesthetic comprises a non-steroidal selected from the group consisting of steroids, salicylates and non-steroidal anti-inflammatory drugs.

19. The method of claim 11 further comprising vitamin A palmitate.

* * * * *